US010317357B2

(12) United States Patent
Le Neel et al.

(10) Patent No.: US 10,317,357 B2
(45) Date of Patent: Jun. 11, 2019

(54) INTEGRATED MULTI-SENSOR MODULE

(71) Applicant: STMicroelectronics Pte Ltd., Singapore (SG)

(72) Inventors: Olivier Le Neel, Singapore (SG); Ravi Shankar, Singapore (SG); Suman Cherian, Singapore (SG); Calvin Leung, Singapore (SG); Tien-Choy Loh, Singapore (SG); Shian-Yeu Kam, Singapore (SG)

(73) Assignee: STMicroelectronics Pte Ltd., Singapore (SG)

( * ) Notice: Subject to any disclaimer, the term of this patent is extended or adjusted under 35 U.S.C. 154(b) by 0 days.

(21) Appl. No.: 16/128,076

(22) Filed: Sep. 11, 2018

(65) Prior Publication Data
US 2019/0025236 A1    Jan. 24, 2019

Related U.S. Application Data

(60) Continuation of application No. 15/605,825, filed on May 25, 2017, now Pat. No. 10,094,797, which is a
(Continued)

(51) Int. Cl.
*G01K 7/18* (2006.01)
*G01N 27/22* (2006.01)
(Continued)

(52) U.S. Cl.
CPC ............ *G01N 27/223* (2013.01); *G01K 7/01* (2013.01); *G01K 7/16* (2013.01); *G01K 7/186* (2013.01);
(Continued)

(58) Field of Classification Search
CPC ......... G01L 19/0092; G01L 9/12; G01K 7/01; G01K 7/20; G01K 7/186; H01L 27/0248; H01L 27/233; H01L 29/7804
(Continued)

(56) References Cited

U.S. PATENT DOCUMENTS 4,608,232 A    8/1986 Sunano et al.
4,938,053 A    7/1990 Jepson et al.
(Continued)

FOREIGN PATENT DOCUMENTS

CN    201307027 Y    9/2009
CN    102680016 A    9/2012
(Continued)

OTHER PUBLICATIONS

Wilson et al., "APTI Course 435 Atmospheric Sampling Student Manual: ," United States Environmental Protection Agency, Air Pollution Training Institute, Research Triangle Park, N.C., Chapter 3, Air measuring instruments, pp. 3-1 to 3-56, Sep. 1980, 61 Pages.
(Continued)

*Primary Examiner* — Long K Tran
(74) *Attorney, Agent, or Firm* — Seed IP Law Group LLP (57) ABSTRACT

A semiconductor-based multi-sensor module integrates miniature temperature, pressure, and humidity sensors onto a single substrate. Pressure and humidity sensors can be implemented as capacitive thin film sensors, while the temperature sensor is implemented as a precision miniature Wheatstone bridge. Such multi-sensor modules can be used as building blocks in application-specific integrated circuits (ASICs). Furthermore, the multi-sensor module can be built on top of existing circuitry that can be used to process signals from the sensors. An integrated multi-sensor module that uses differential sensors can measure a variety of localized ambient environmental conditions substantially simultaneously, and with a high level of precision. The multi-sensor module also features an integrated heater that can be used to calibrate or to adjust the sensors, either automatically or as needed. Such a miniature integrated multi-sensor module that features low power consumption
(Continued)

can be used in medical monitoring and mobile computing, including smart phone applications.

13 Claims, 12 Drawing Sheets

Related U.S. Application Data continuation of application No. 14/887,145, filed on Oct. 19, 2015, now Pat. No. 9,689,824, which is a division of application No. 13/853,732, filed on Mar. 29, 2013, now Pat. No. 9,176,089.

(51) Int. Cl.
| | |
|---|---|
| H01L 25/00 | (2006.01) |
| H01L 25/065 | (2006.01) |
| H01L 29/78 | (2006.01) |
| H01L 27/02 | (2006.01) |
| G01L 19/00 | (2006.01) |
| G01L 9/12 | (2006.01) |
| G01K 7/20 | (2006.01) |
| G01K 7/16 | (2006.01) |
| G01K 7/01 | (2006.01) |
| G01D 21/02 | (2006.01) |

(52) U.S. Cl.
CPC ............ *G01K 7/20* (2013.01); *G01L 9/12* (2013.01); *G01L 19/0092* (2013.01); *H01L 25/0652* (2013.01); *H01L 25/50* (2013.01); *H01L 27/0248* (2013.01); *H01L 29/7804* (2013.01); *G01D 21/02* (2013.01); *H01L 2924/0002* (2013.01)

(58) Field of Classification Search
USPC ................. 257/415, 417, 470; 438/48, 50
See application file for complete search history.

(56) References Cited

U.S. PATENT DOCUMENTS

| | | | |
|---|---|---|---|
| 5,834,777 | A | 11/1998 | Wong |
| 6,243,474 | B1 | 6/2001 | Tai et al. |
| 6,322,247 | B1 | 11/2001 | Bonne et al. |
| 6,352,874 | B1 | 3/2002 | McNeil et al. |
| 6,361,206 | B1 | 3/2002 | Bonne |
| 6,383,832 | B1 | 5/2002 | Nakabayashi |
| 6,478,974 | B1 | 11/2002 | Lebouitz et al. |
| 6,546,812 | B2 | 4/2003 | Lewis |
| 6,681,623 | B2 | 1/2004 | Bonne et al. |
| 6,698,297 | B2 | 3/2004 | Gysling |
| 6,879,089 | B2 | 4/2005 | Wong et al. |
| 7,280,436 | B2 | 10/2007 | Pedersen |
| 7,437,951 | B2 | 10/2008 | McDonald et al. |
| 7,556,895 | B2 | 7/2009 | Moriya et al. |
| 7,703,339 | B2 | 4/2010 | Sulouff, Jr. et al. |
| 7,821,085 | B2 | 10/2010 | Suzuki et al. |
| 7,864,403 | B2 | 1/2011 | Bita et al. |
| 7,880,315 | B2 | 2/2011 | Beyne et al. |
| 7,946,505 | B2 | 5/2011 | Lynam et al. |
| 8,062,497 | B2 | 11/2011 | Witvrouw et al. |
| 8,258,017 | B2 | 9/2012 | Masuko et al. |
| 8,390,121 | B2 | 3/2013 | Okumura et al. |
| 8,487,387 | B2 | 7/2013 | Lin et al. |
| 8,696,989 | B2 | 4/2014 | Esfandyarpour et al. |
| 8,715,514 | B2 | 5/2014 | Lee et al. |
| 8,806,933 | B2 | 8/2014 | Kohno et al. |
| 8,852,513 | B1 | 10/2014 | Speer et al. |
| 9,000,542 | B2 | 4/2015 | Loh et al. |
| 9,082,681 | B2 | 7/2015 | Le Neel et al. |
| 9,105,479 | B2 | 8/2015 | Besling et al. |
| 9,164,052 | B1 | 10/2015 | Speer et al. |
| 9,234,876 | B2 | 1/2016 | Le Neel et al. |
| 9,317,155 | B2 | 4/2016 | Magi |
| 9,618,653 | B2 | 4/2017 | Le Neel et al. |
| 2002/0160611 | A1 | 10/2002 | Horsley |
| 2002/0166376 | A1 | 11/2002 | Kohmura et al. |
| 2003/0079542 | A1 | 5/2003 | Bonne et al. |
| 2005/0109081 | A1 | 5/2005 | Zribi et al. |
| 2006/0162466 | A1 | 7/2006 | Wargo et al. |
| 2006/0270238 | A1 | 11/2006 | Izumi et al. |
| 2008/0163687 | A1 | 7/2008 | Kranz et al. |
| 2008/0194053 | A1 | 8/2008 | Huang |
| 2008/0308920 | A1 | 12/2008 | Wan |
| 2008/0315332 | A1 | 12/2008 | Kaelberer et al. |
| 2009/0218702 | A1 | 9/2009 | Beyne et al. |
| 2010/0173437 | A1 | 7/2010 | Wygant et al. |
| 2010/0314740 | A1 | 12/2010 | Choi et al. |
| 2011/0031565 | A1 | 2/2011 | Marx et al. |
| 2011/0045639 | A1 | 2/2011 | Masuko et al. |
| 2011/0108932 | A1 | 5/2011 | Benzel et al. |
| 2011/0150261 | A1 | 6/2011 | Ho et al. |
| 2011/0298134 | A1 | 12/2011 | Williams et al. |
| 2012/0024054 | A1 | 2/2012 | Huang et al. |
| 2012/0032283 | A1 | 2/2012 | Frey et al. |
| 2012/0144921 | A1 | 6/2012 | Bradley et al. |
| 2012/0167392 | A1 | 7/2012 | Cherian et al. |
| 2012/0168882 | A1 | 7/2012 | Cherian et al. |
| 2012/0171713 | A1 | 7/2012 | Cherian et al. |
| 2012/0171774 | A1 | 7/2012 | Cherian et al. |
| 2012/0299127 | A1 | 11/2012 | Fujii et al. |
| 2013/0010826 | A1 | 1/2013 | Le Neel et al. |
| 2013/0036806 | A1 | 2/2013 | Kohno |
| 2013/0106813 | A1 | 5/2013 | Hotelling et al. |
| 2013/0139587 | A1 | 6/2013 | Le Neel et al. |
| 2013/0334620 | A1 | 12/2013 | Chu et al. |
| 2014/0120401 | A1 | 5/2014 | Shin et al. |
| 2014/0147705 | A1 | 5/2014 | Wang et al. |
| 2014/0197500 | A1 | 7/2014 | Guillemet et al. |
| 2014/0264655 | A1 | 9/2014 | Williams et al. |
| 2014/0264744 | A1 | 9/2014 | Chu et al. |
| 2014/0268523 | A1 | 9/2014 | Gogoi |
| 2014/0291677 | A1 | 10/2014 | Le Neel et al. |
| 2014/0294046 | A1 | 10/2014 | Le Neel et al. |
| 2014/0311905 | A1 | 10/2014 | Stetter et al. |

FOREIGN PATENT DOCUMENTS

| | | | |
|---|---|---|---|
| CN | 102680018 A | | 9/2012 |
| CN | 101788315 B | | 11/2012 |
| CN | 202770456 U | | 3/2013 |
| TW | 200531124 A | * | 3/2004 |
| TW | 200531124 A | | 9/2005 |

OTHER PUBLICATIONS

Lim et al., "The humidity effect on air flow rates in a critical flow venturi nozzle," *Flow Measurement and Instrumentation* 22:402-405, Jun. 4, 2011.

\* cited by examiner

INTEGRATED MULTI-SENSOR MODULE

BACKGROUND

Technical Field

The present disclosure relates to the fabrication of application-specific integrated circuits (ASICs) that incorporate thin film environmental sensors.

Description of the Related Art

Mobile computing devices such as smart phones typically include embedded electronic sensors such as, for example, magnetic field sensors (magnetometers) that can be used to determine orientation of the smart phone relative to the earth's ambient magnetic field. In addition, smart phones typically contain one or more accelerometers that sense the acceleration of gravity directed perpendicular to the earth's surface, and can detect movement of the smart phone. However, smart phones available today generally do not offer to consumers or program developers features that entail sensing, monitoring, or controlling local environmental conditions. Providing additional environmental sensors within smart phones, tablet computers, and the like, may encourage program developers to create applications that otherwise might not be possible.

Some existing products contain miniature environmental sensors. For example, electronic climate control devices (e.g., thermostats) rely on electronic sensors to trigger activation of furnaces and air conditioners for feedback control of air temperature and humidity. Electronic weather stations also rely on internal temperature sensors, barometric pressure sensors, and humidity sensors, such as, for example, those described in U.S. patent application Ser. No. 13/310,477 to LeNeel et al. Typically, these miniature environmental sensors are fabricated on separate substrates (dies) from one another, or the sensors are built on one substrate and associated circuitry for signal processing and control is fabricated on a separate die (see, for example, US Patent Application Publication 2012/0171774A1 to Cherian et al.). Separate fabrication processes have been necessary because integrating more than one type of environmental sensor on the same substrate, with circuitry, poses a significant challenge.

In some applications, chemical sensors have been integrated with circuitry for analyzing a chemical sample (see, for example, US Patent Application Publication 2012/0171713A1 to Cherian et al.). In other applications, chemical sensors can be built into a vehicle for delivering to the micro-sensor a chemical or biological sample for analysis, such as a razor blade (see, for example, US Patent Application Publication 2012/0167392A1 to Cherian et al.) In further applications, it has been possible to integrate temperature and humidity environmental sensors with the chemical sensors, for example, as disclosed in U.S. Patent Application Publication US 2012/0168882 to Cherian et al. However, in general, integration of multiple environmental sensors, including fluid sensors for measuring fluid pressure and flow rates, has been challenging because sensing elements for different environmental conditions typically require different, or even incompatible, materials.

It is noted that the references cited above are owned by the applicants of the present patent application, and are hereby incorporated by reference in their entirety.

BRIEF SUMMARY

A solution described herein addresses these challenges by integrating temperature, pressure, and humidity sensors onto a single semiconductor die to provide a multi-sensor module. One or more such multi-sensor modules can be used as building blocks in application-specific integrated circuits (ASICs). Furthermore, the multi-sensor module can be built on top of existing circuitry that can be used to process signals from the sensors. The integrated multi-sensor module described herein permits a variety of ambient environmental conditions to be measured at substantially the same time and location, with a high level of precision.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

It will be appreciated that, although specific embodiments of the present disclosure are described herein for purposes of illustration, various modifications may be made without departing from the spirit and scope of the present disclosure. Accordingly, the present disclosure is not limited except as by the appended claims.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to insulating materials or semiconducting materials can include various materials other than those used to illustrate specific embodiments of the transistor devices presented. The term "environmental sensors" should not be construed narrowly to mean only sensors for pressure, temperature, and humidity, for example, but rather, the term "environmental sensors" is broadly construed to cover any type of sensor that is capable of monitoring ambient characteristics.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, include a spin-expose-develop process sequence involving a photoresist. Such a photolithography sequence entails spinning on the photoresist, exposing areas of the photoresist to ultraviolet light through a patterned mask, and developing away exposed (or alternatively, unexposed) areas of the photoresist, thereby transferring a positive or negative mask pattern to the photoresist. The photoresist mask can then be used to etch the mask pattern into one or more underlying films. Typically, a photoresist mask is effective if the subsequent etch is relatively shallow, because photoresist is likely to be consumed during the etch process. Otherwise, the photoresist can be used to pattern a hard mask, which in turn, can be used to pattern a thicker underlying film.

Reference throughout the specification to conventional etching techniques known in the art of semiconductor fabrication for selective removal of polysilicon, silicon nitride, silicon dioxide, metals, photoresist, polyimide, or similar materials include such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to examples of integrated micro-sensors that have been produced; however, the present disclosure and the reference to certain materials, dimensions, and the details and ordering of processing steps are exemplary and should not be limited to those shown.

In the figures, identical reference numbers identify similar features or elements. The sizes and relative positions of the features in the figures are not necessarily drawn to scale.

Figure 1A:
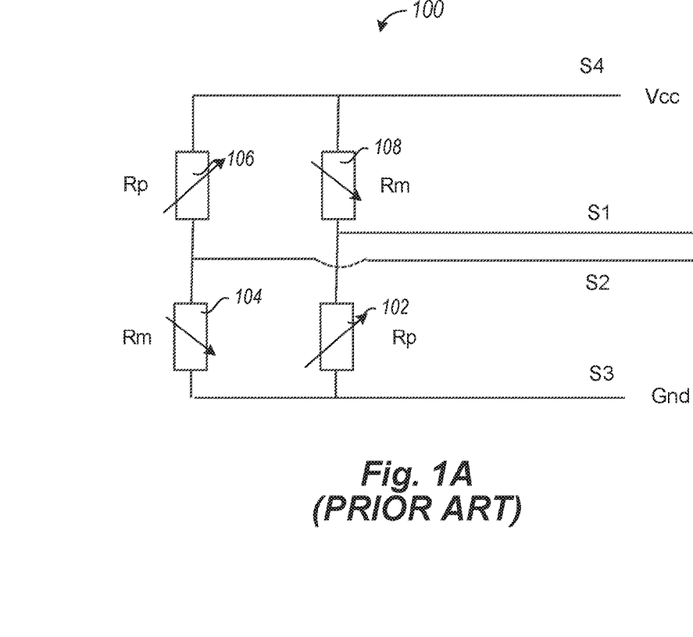
FIG. 1A is schematic diagram of a conventional Wheatstone bridge.

FIG. 1A is a schematic of a standard, prior art, Wheatstone bridge circuit 100. The Wheatstone bridge configuration shown is commonly used to measure an unknown resistance 102 between S1 and S3 by adjusting a variable resistance 104. The resistance measurement is based on comparison of the ratio of resistances on the left side of the Wheatstone bridge compared to the ratio of resistances on the right side of the Wheatstone bridge, where $V_{out}=V_{CC}(R_m-R_p)/(R_m+R_n)$. If the resistance ratios $R_m/R_p$ on the right, and $R_p/R_m$ on the left are balanced, the voltage difference between S1 and S2 will be zero. If the resistance ratios are not equal, the voltage $V_{out}$ between S1 and S2 will be non-zero and the value of variable resistance 104 ($R_m$) can then be adjusted to produce a zero voltage at $V_{out}$. The resistance $R_p$ is positively correlated with temperature such that $R_p$ increases as the temperature increases, while the resistance $R_m$ is negatively correlated with temperature such that $R_m$ decreases as temperature increases. The Wheatstone bridge as shown in FIG. 1A is implemented herein on a silicon substrate along with other sensors as described below to provide precise temperature measurements with a fast response time. While a Wheatstone bridge configuration is desirable because it offers enhanced precision, the present disclosure can additionally or alternatively include a resistive temperature detector (RTD) type sensor, for example, that can use a platinum (Pt) sensing element.

Figure 1B:
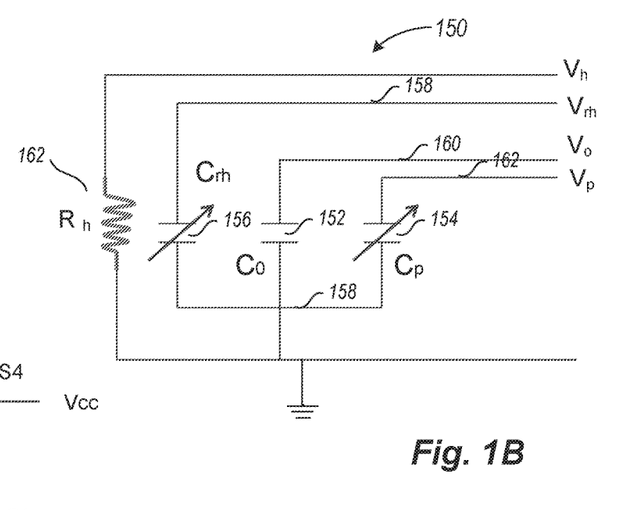
FIG. 1B is a schematic diagram of a differential capacitor circuit that may be implemented on a semiconductor substrate as described herein.

FIG. 1B shows a differential capacitance circuit 150 that includes three parallel plate capacitors for use as ambient environmental sensors: $C_p$ for measuring pressure, $C_0$ for use as a reference pressure sensor, and $C_{rh}$ for measuring relative humidity. In the example shown, $C_p$ and $C_{rh}$ have variable capacitance values, while $C_0$ is shown as having a fixed value of capacitance. An output voltage $V_{rh}$ characterizes an output signal 158 that indicates ambient relative humidity as measured by the differential capacitor $C_{rh}$; an output voltage $V_o$ characterizes an output signal 160 that indicates a reference pressure as measured by the differential capacitor $C_o$; and an output voltage $V_p$ characterizes an output signal 162 that indicates ambient pressure as measured by the differential capacitor $C_p$. The three capacitors $C_p$, $C_o$, and $C_{rh}$ can be connected to a common reference terminal that may be grounded.

The Wheatstone bridge and the capacitive sensors shown in FIGS. 1A and 1B, respectively, can be accompanied by a resistive heater 162. The addition of the resistive heater 162 is important because environmental and biomedical species being sensed are influenced by temperature. For example, ambient humidity depends on temperature; moisture content within a polyimide film is temperature-dependent; gas pressure and concentrations are temperature dependent in accordance with the ideal gas law, PV=nRT; and chemical reactions are also generally temperature dependent in accordance with the Arrehnius law. The resistive heater 162 has an associated resistance $R_h$, which can be energized by applying a voltage $V_h$. For example, the heater 162 can be integrated with the three capacitors $C_p$, $C_o$, and $C_{rh}$ as a common structural element, so as to influence the readings of all three devices substantially simultaneously. Or, the heater 162 can be implemented separately from, but desirably in proximity to, the sensors. The resistive heater 162 can further be used as a reset device to recondition a sensor following exposure to an extreme environment. For example, the resistive heater 162 can recondition a saturated humidity sensor 156 by driving moisture out of the dielectric thin film through evaporation, thereby restoring accurate performance of the sensor. The heater 162 can further be used as a calibration/test device as described in further detail below. Use of such a resistive heater 162 can enhance precision and reproducibility of sensors, in comparison with sensors that lack such an on-board calibration device. Desirably, such calibration testing can be implemented as an automatic feature of a mobile device in which the sensors are deployed. For example, a user can perform a smart phone calibration test daily to ensure the humidity sensor is still functional. In these applications, the heater 162 raises the local temperature to a value that is typically at or below about 100 C. Additionally or alternatively, the heater 162 can be used to adjust, or tune, the properties of the dielectric thin film. In this case, the heater 162 can be pulsed in a controlled fashion for millisecond-long pulses to raise the temperature from about 100 C to as high as about 800 C.

Figure 2:
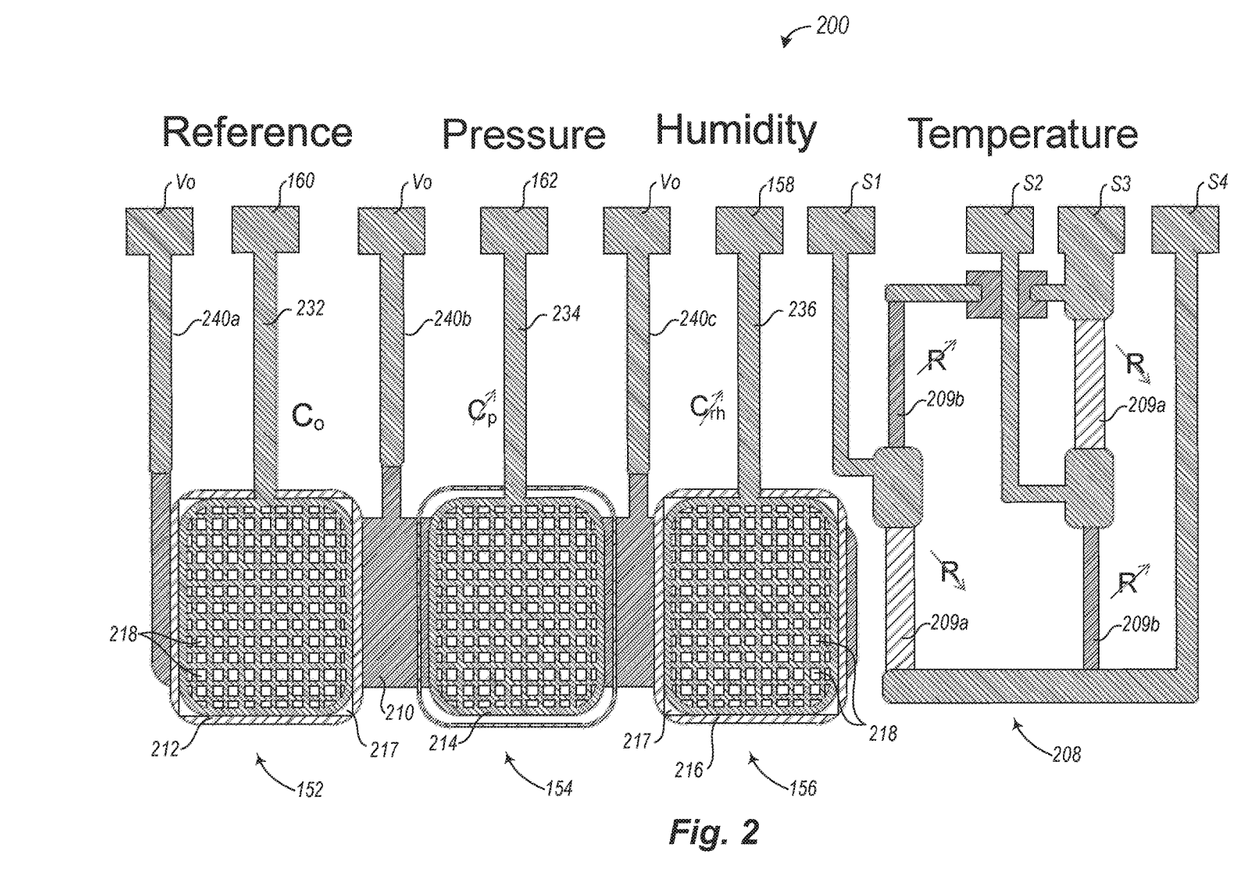
FIG. 2 is a plan view of a circuit layout for an integrated multi-sensor module as described herein, according to one embodiment.

The Wheatstone bridge shown in FIG. 1A and the differential capacitors shown in FIG. 1B, along with the resistive heater 162, can be implemented as components of a semiconductor-based multi-sensor module 200. FIG. 2 shows a top-down view of the semiconductor-based multi-sensor module 200, according to an exemplary embodiment. In the example shown, the multi-sensor module 200 includes four sensors co-located on a common silicon substrate: the reference pressure sensor 152, the pressure sensor 154, the humidity sensor 156, and the Wheatstone bridge 100 implemented as a temperature sensor 208. However, the multi-sensor module 200 is not limited to such a configuration. For example, other embodiments can include a different arrangement of sensors than the one shown. In still other embodiments, a different number of sensors may be included, or sensors of different types than those shown.

The temperature sensor 208 can be laid out as an integrated Wheatstone bridge circuit corresponding to the schematic shown in FIG. 1A, in which contacts for receiving the sensor signals S1, S2, S3, S4 shown in FIG. 2 correspond to those shown in FIG. 1A. The resistors denoted as $R_m$ in FIG. 1A are indicated in FIG. 2 by a decreasing arrow to show that they have a negative thermal coefficient of resistance (TCR) such that their resistance varies inversely with temperature (i.e., resistance decreases as temperature increases). The resistors denoted as $R_p$ have a positive TCR such that their resistance increases as temperature increases. The Wheatstone bridge so configured can be balanced if the TCR values of the two different materials used to form the resistive elements 209a and 209b are equal and opposite. To ensure that the resistive elements are highly temperature-sensitive, a TCR value having a magnitude of about 3000 is desirable.

The three parallel plate capacitor sensors 152, 154, 156 correspond to the differential capacitors $C_0$, $C_p$, $C_{rh}$, respectively, shown in FIG. 1B. As shown in FIG. 2, the three parallel plate capacitor sensors 152, 154, 156 are configured with metal mesh top plates 212, 214, 216, respectively, while they share a common bottom plate 210 made of a substantially solid, continuous, piece of metal. Disposed between the metal mesh top plates 212, 216 and the common bottom plate 210, for each parallel plate capacitor sensor, is a thin capacitive dielectric film 217 that is sensitive to ambient environmental conditions. A purpose of the metal mesh top plates 212, 214, 216 is to provide continuous exposure of the dielectric film 217 to the same ambient environment through 1-2 µm wide openings 218 in the mesh. When the capacitive dielectric film 217, or membrane, is exposed to the environment, pressure on the membrane decreases the membrane thickness, thereby changing the capacitance of the sensor device. Similarly, changes in ambient humidity can cause the capacitive dielectric film 217 to expand or contract, thereby changing the membrane thickness, and in turn the capacitance of the sensor. The pressure sensor capacitor $C_p$ does not include the capacitive dielectric film 217.

Interconnect circuitry configured to extract signals from the multi-sensor module 200 can include a reference sensor interconnect 232, a pressure sensor interconnect 234, and a humidity sensor interconnect 236, each of which can extract signals from the metal mesh top plates 212, 214, 216, respectively. In addition, heater interconnects 240a, 240b, 240c can access the common bottom plate 210, which serves as a hot plate for performing sensor calibration tests, either pre-programmed in an auto-test mode, or on an as-needed basis.

Figure 3:
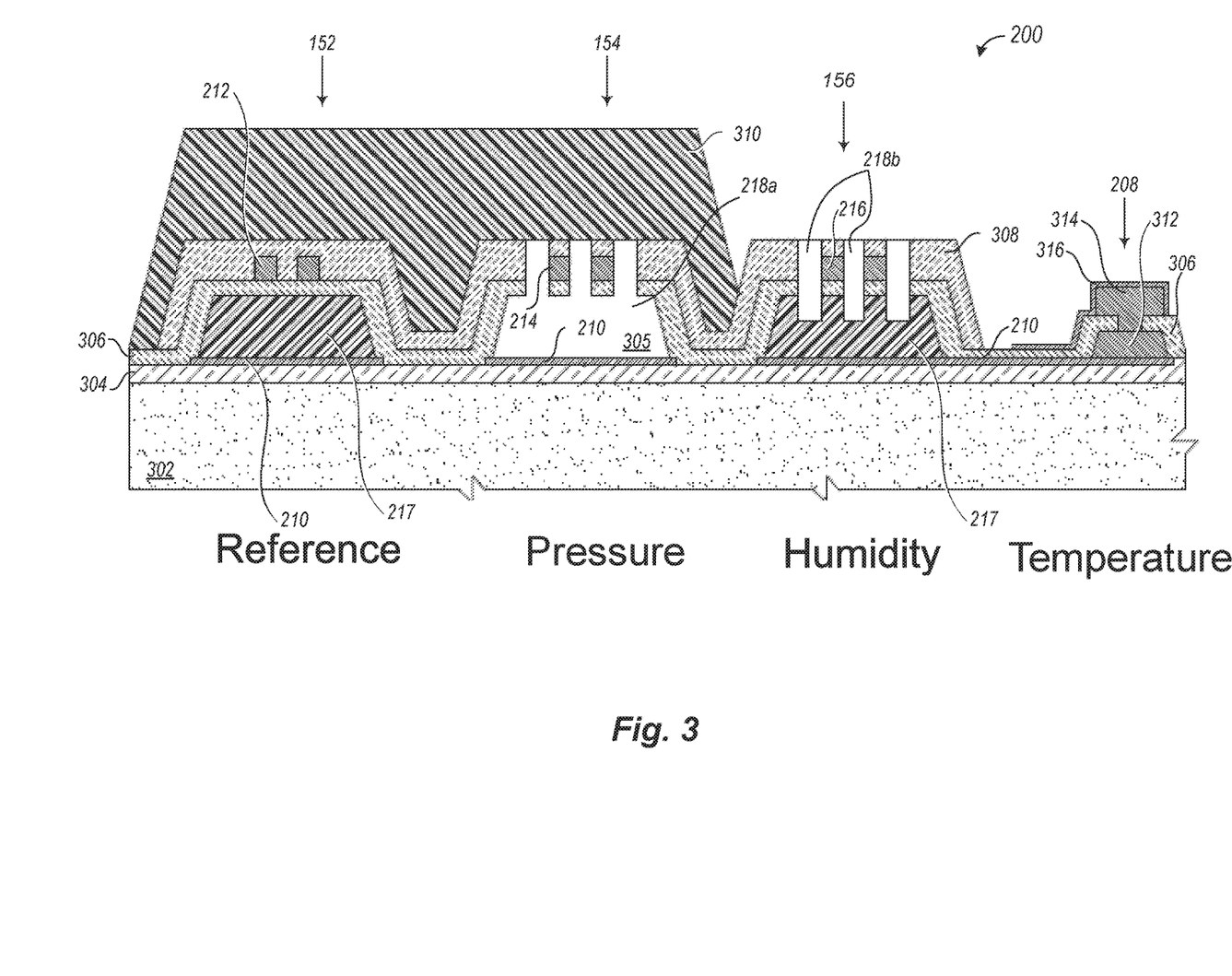
FIG. 3 is a cross-section taken along lines 3-3, of the circuit shown in FIG. 2.

FIG. 3 shows a side view of the multi-sensor module 200 shown in FIG. 2, including the reference pressure sensor 152, pressure sensor 154, relative humidity sensor 156, and temperature sensor 208. Each sensor includes one or more thin film sensing elements designed to be highly sensitive to environmental conditions. The temperature sensor 208 is designed to be accurate to within about ±1 degree; the relative humidity sensor 156 is designed to be accurate to within about ±3%; and the pressure sensors 152 and 154 are designed to be accurate to within about ±1 mbarr. Choice of materials for the various structures shown in FIG. 3 can determine the degree of success of integrating the various sensors onto a common substrate.

The multi-sensor module 200 can be built on a non-active substrate 302 that is made of, for example, crystalline silicon, amorphous silicon (glass), or polysilicon. Alternatively, the multi-sensor module 200 can be built on top of active silicon devices in a monocrystalline silicon substrate. For example, underlying logic circuitry, including transistors formed in the silicon substrate, can be configured to read and process sensor signals generated by the multi-sensor module 200. It is generally advantageous for the substrate 302 to be thermally stable so as to act as a thermal barrier to protect the multi-sensor module 200 from heat generated by surrounding active circuitry. An insulating oxide layer 304 can be deposited on the surface of the substrate 302, to a thickness of about 2 microns to further separate the multi-sensor module 200 from the substrate 302.

Differential capacitor elements within the multi-sensor module 200 include, as components, the common bottom plate 210, one or more environmentally sensitive capacitive dielectric films 217, and metal mesh top plates 212, 214, 216. The common bottom plate 210, which acts as a heating element, is desirably made of a refractory metal having a low thermal coefficient of resistance (TCR) such as tantalum aluminum (TaAl), titanium (Ti), or tungsten silicon nitride (WSiN). Such materials are advantageous because they can withstand changing temperatures throughout a wide range of several hundred to several thousand degrees Celsius. In addition, such materials exhibit a medium sheet resistance so they can dissipate hot spots that can develop, at which temperatures can exceed 1000 C. Alternatively, the common bottom plate (heater) can be made of platinum so that the same material can be used for both sensing and heating. The metal mesh top plates 212, 214, 216 can be made of aluminum, or another suitable metal.

The desired material for the capacitive dielectric film 217 in the example shown is a 1-4 um thick layer of polyimide for both the humidity sensor 156 and the reference pressure sensor 152. It is generally advantageous to use the thinnest possible capacitive dielectric film 217 (e.g., 1 μm) to reduce topography, thus producing a smoother surface. The desired material for the capacitive dielectric film 217 used in the pressure sensor 154 shown is air (i.e., the dielectric is formed as a cavity 305 that can be filled by the passage of ambient air through the openings 218a in the mesh top plate 214).

Between each capacitive dielectric film 217 and metal mesh top plate there can be formed a second dielectric layer 306 of, for example, about 0.5 μm of silicon nitride ($Si_3N_4$) or silicon carbide (SiC), to provide thermal transmission so as to readily dissipate heat. Surrounding the metal mesh top plates, there can be deposited a third dielectric passivation layer 308 of, for example, 0.5 μm-thick silicon nitride ($Si_3N_4$). In accordance with the embodiment shown, the dielectric/metal/passivation total stack height in the embodiment shown is about 1 μm. The width of the second and third (passivation) dielectrics between the metal mesh regions and the neighboring openings shown is also about 1 μm. The second dielectric layer 306 and the metal mesh top plate 214 over the pressure sensor act as a floating membrane that expands and contracts with pressure inside the opening 218a.

Finally, a thick protective layer 310, shown in FIG. 3 as a polyimide film having a thickness of about 6 μm, can be spun on at room temperature to cover the reference pressure sensor 152. An optional silicon nitride (SiN).cap can be deposited to shield the photo-sensitive polyimide protective layer 310 from exposure to light.

The temperature sensor 208 within the integrated multi-sensor module 200 includes exemplary multi-layer resistive elements, one of which is shown in cross section at the far right of FIG. 3. Each resistive element can be made up of layers that can include the common bottom plate 210, a second metal layer 312, the second dielectric layer 306, and a third metal layer 314. The second metal layer 312 can be made of, for example, AlCu. The third metal layer can be made of, for example, aluminum that can be capped with a thin, high TCR metal such as a platinum (Pt) cap layer 316 of about 100 Å. Alternatively, the cap layer 316 can be made of a chromium silicon (CrSi) material, which also has a high TCR.

Figures 4A, 4B:
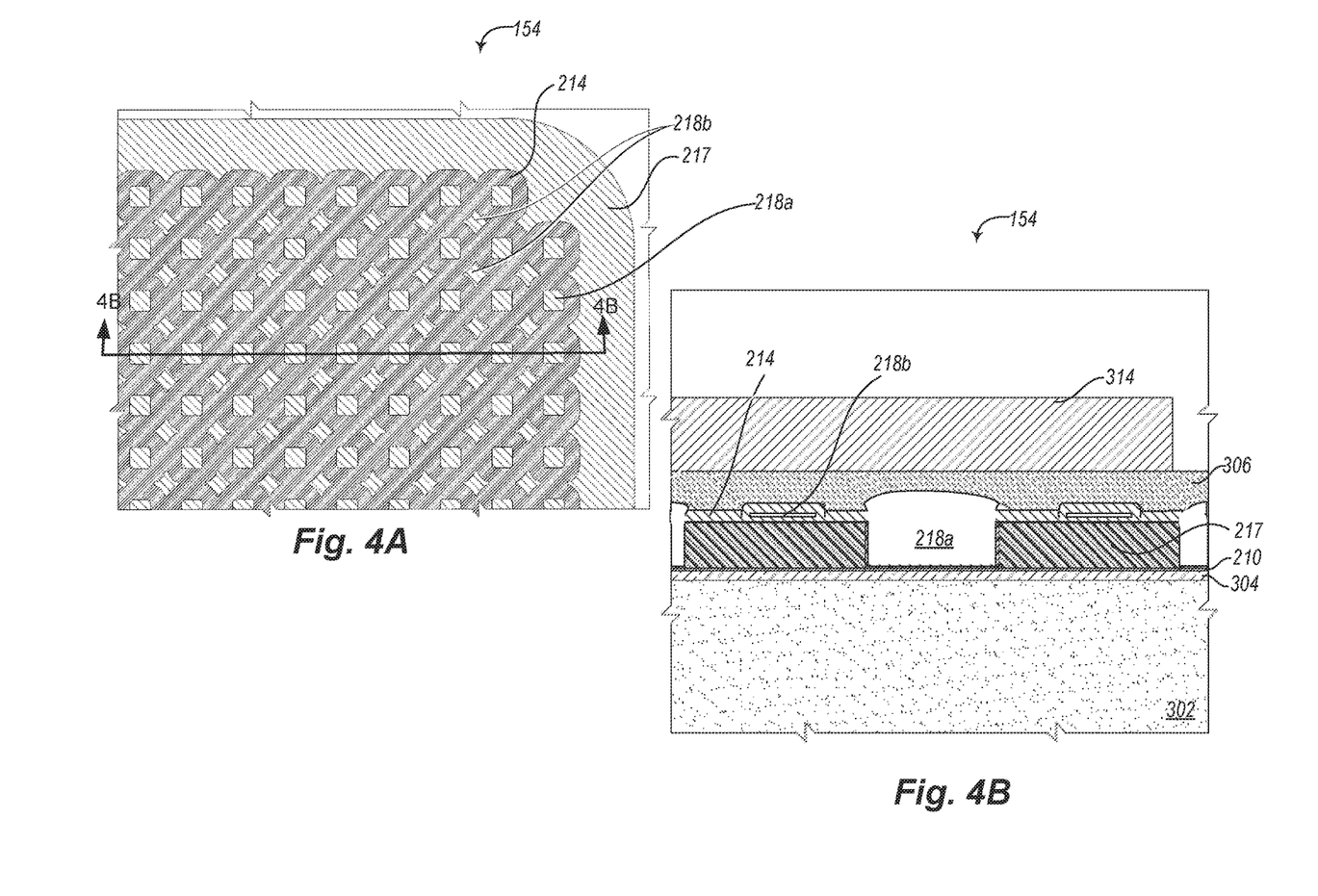
FIG. 4A is a plan view of a pressure sensing element, according to one embodiment.
FIG. 4B is a cross-sectional view of the pressure sensing element shown in FIG. 4A, along cut lines 4-4

FIGS. 4A and 4B show detailed, magnified views of a representative capacitive environmental sensor, for example, the pressure sensor 154. A top-down magnified view of one corner of the metal mesh top plate 214 is shown in FIG. 4A. In one embodiment, square and diamond-shaped openings 218a and 218b, respectively, arranged in a matrix, are shown surrounded by the metal mesh top plate 214. The polyimide film 217 remains underneath the diamond-shaped openings 218b which correspond to the reference pressure sensors 152 and the humidity sensors 156. However the polyimide film 217 is removed from the square-shaped openings 218a, which correspond to the pressure sensors 154. The underlying capacitive dielectric 217 is visible through both the openings 218a and 218b.

FIG. 4B represents a side view of the pressure sensor 154 as it appears on a scanning electron micrograph taken at 3000× magnification. The top layer, according to an exemplary embodiment, is the third metal layer 314. Underneath the third metal layer 314 is shown the 500 nm thick silicon nitride layer 306. The metal mesh top plate 214 extends between each of the openings 218a. The diamond-shaped openings 218b are located in a plane behind the cut plane 4-4. The third metal layer 314 and the silicon nitride layer 306 together form a membrane that is anchored on the metal mesh top plate 214 between the square-shaped openings 298a. Over the square-shaped openings, however, the membrane floats in response to pressure variations, wherein the capacitive dielectric 217, in this case, polyimide, has been removed by etching, for example, using an oxygen-based dry etch. Underneath the polyimide capacitive dielectric 217 is shown the common bottom plate 210, which rests on the thick insulating oxide 304, and in turn, on the silicon substrate 302.

Figure 5:
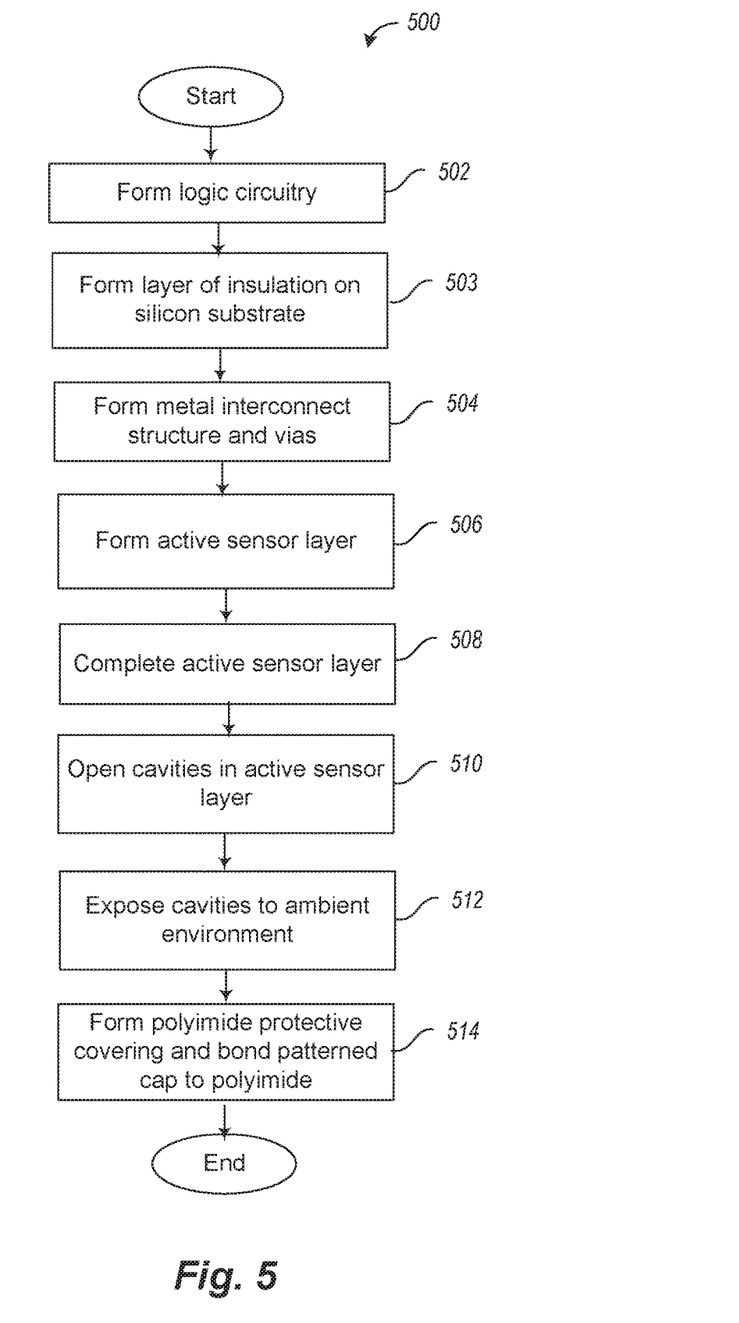
FIG. 5 is a flow diagram illustrating a process for fabricating the multi-sensor module shown in FIGS. 2 and 3.

FIG. 5 presents a high-level process flow 500 that describes basic actions in an exemplary fabrication process that can be used to create the structures shown in FIGS. 2, 3, 4A, and 4B. In general, constraints exist on the process temperatures at most steps in the process flow 500, due to the presence of polyimide thin films and other delicate materials. These include very thin films of only a few nm used as membranes to sense environmental humidity, pressure, and temperature. Thermal treatment and stress of post-processing can have a significant effect on film performance. Processing temperatures below about 300 C are typically safe for polyimide thin films. Different formulations of polyimide may be used at different steps, and the presence or parameters of polyimide cure steps can also be varied to reduce shrinkage as solvents tend to outgas from the polyimide film at higher temperatures.

At 502, logic circuitry can be optionally fabricated underneath the active sensor layer to process sensor signals.

At 503, a layer of insulation such as the oxide layer 304 can be formed on the silicon substrate 302. Alignment marks can be patterned in the oxide to assist in alignment of subsequent layers.

At 504, a metal interconnect structure can be formed, including at least two patterned layers of metal separated by an inter-layer dielectric (ILD). First, a low TCR metal layer, the common bottom plate 210, can be deposited and patterned using a dry chlorine etch. A second metal layer 312 can then be deposited and patterned using a wet etch to form resistive elements making up the temperature sensor 208. Next, a photo-sensitive film such as polyimide can be spun on using a spin coater, and can then be patterned using conventional photolithography techniques as described above.

At 506, the first dielectric layer 217 can be deposited and patterned to etch vias between the first and second metal layers. The first dielectric layer 217 provides the dielectric between the capacitor plates of the differential capacitive sensors 152, 154, 156. Following the via etch, the third metal layer 314 can be deposited and patterned using standard metal deposition and photolithography techniques.

At 508, formation of the active sensors can be completed. The second dielectric layer 306 can be deposited and patterned using standard thin film deposition, photolithography, and conventional via etch techniques. Next, thin film resistor (TFR) connectors can be formed, from which signals S1, S2, S3, S4 can be obtained. A conventional metal deposition process can be used, with close control of the deposition time to produce a 5-10 nm thick film. Next, the actual TFR temperature sensors can be patterned.

At 510, the dielectric 217 can be removed from the pressure sensor 154 to form the void 305, thus opening a cavity in the active sensor layer. This can be done by partially etching the dielectric 217 using an isotropic $O_2$ plasma etch.

At 512, the openings 218 can be etched in the relative humidity sensor 156 to expose the void 305 to the ambient environment.

At 514, the thick protective covering 310 can be formed by deposited and patterning polyimide using a wet etch process. Finally, a silicon nitride cap can be adhesively bonded to the uncured polyimide thick protective covering 310.

Figure 6:
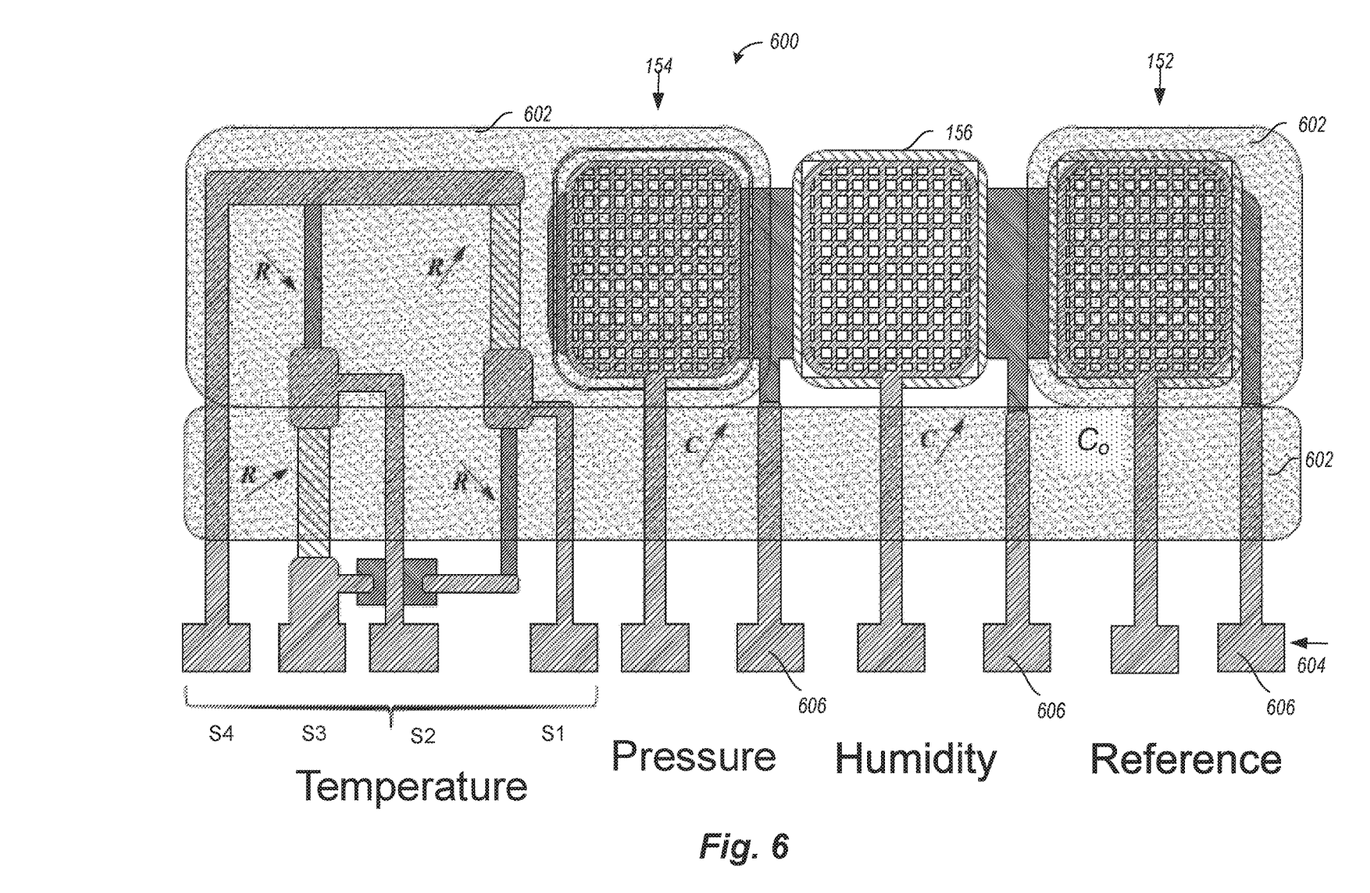
FIG. 6 is a plan view of a single multi-sensor module having an added passivation layer that covers three of the four sensors.

FIG. 6 shows one embodiment of a passivated multi-sensor module 600, over which a patterned passivation layer 602 has been deposited. The passivated multi-sensor module 600 shown is configured such that the humidity sensor 156 and the pressure sensor 154 are in different positions compared with the multi-sensor sensor module 200. In this example, the patterned passivation layer 602 leaves the humidity sensor 156 uncovered so as to allow the dielectric membrane of the humidity sensor 156 ample exposure to ambient moisture variation. The reference sensor 152, labeled "$C_o$," is underneath the patterned passivation layer 602. The patterned passivation layer 602 also exposes a row of electrical contact pads 604 so that signals are accessible to be read from the sensors. A voltage can be applied to contact pads 606 to use the common bottom plate 210 as a heater. The patterned passivation layer 602 can be made of a standard passivation material such as polyimide, for example.

Figure 7A:
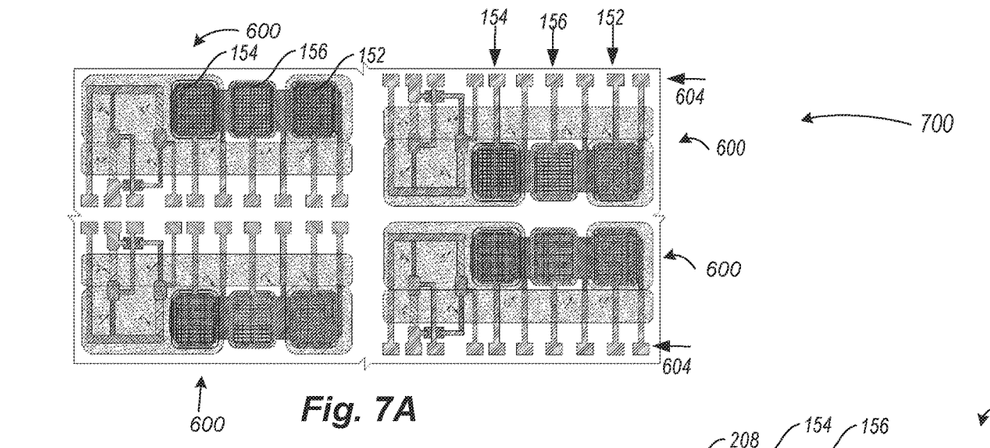
FIG. 7A is a plan view of an area of ASIC layout of four of the multi-sensor modules shown in FIG. 6, having an added passivation layer.

FIG. 7A shows an exemplary ASIC sensor module layout 700 that includes four passivated multi-sensor modules 600, each multi-sensor module having the added passivation layer 602 as shown in FIG. 6. The two passivated multi-sensor modules 600 on the left are in a mirror-image arrangement, as are the two passivated multi-sensor modules 600 on the right. Such a mirror-image arrangement results in greater structural stability after a silicon cap is attached as described below.

Figure 7B:
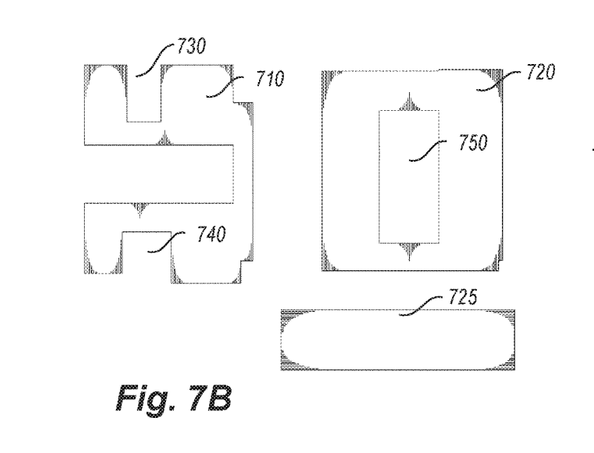
FIG. 7B is a plan view of a patterned silicon cap as described herein.

FIG. 7B shows three exemplary patterned silicon caps 710, 720, 725 for attachment to the exemplary ASIC sensor module layout 700. The patterned silicon caps 710, 720, 725 are silicon substrates, about 300 microns thick, configured with openings 730, 740, 750 that are sized and dimensioned to align with selected sensors. The patterned silicon caps 710, 720, 725 can be adhesively bonded to the layout 700 to form a laminate that protects portions of each multi-sensor module 600 while allowing contact between the sensor membranes and the ambient environment (e.g., air). The passivation layer, for example, a polyimide film or a dry photoresist, can serve as an adhesive if left un-cured until after the bonding is complete. The bonding process is desirably carried out at a low temperature. After bonding, the adhesive layer can be cured in an oxygen environment at a temperature of about 300-350 C.

Figure 7C:
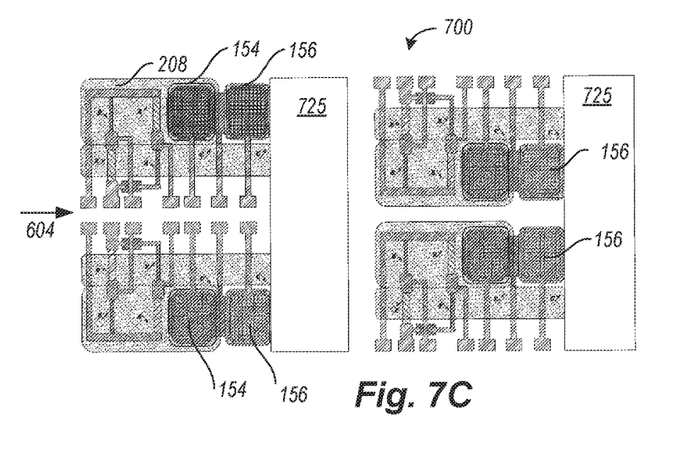
FIG. 7C is a plan view of the patterned silicon cap shown in FIG. 7B, following adhesive bonding to the four multi-sensor modules shown in FIG. 7A.

FIG. 7C shows the silicon caps 725 attached to the ASIC sensor module layout 700. The silicon caps 725 expose the temperature sensors 208, the pressure sensors 154, the humidity sensors 156, and the rows of electrical contact pads 604. In the example shown, only the reference pressure sensors 152 are covered by the silicon caps 725. Because the openings are needed for sensing ambient environmental conditions, the final product is essentially environmentally unprotected. In other embodiments, depending on the application, the silicon caps 725 may align with different sensors.

Figure 8:
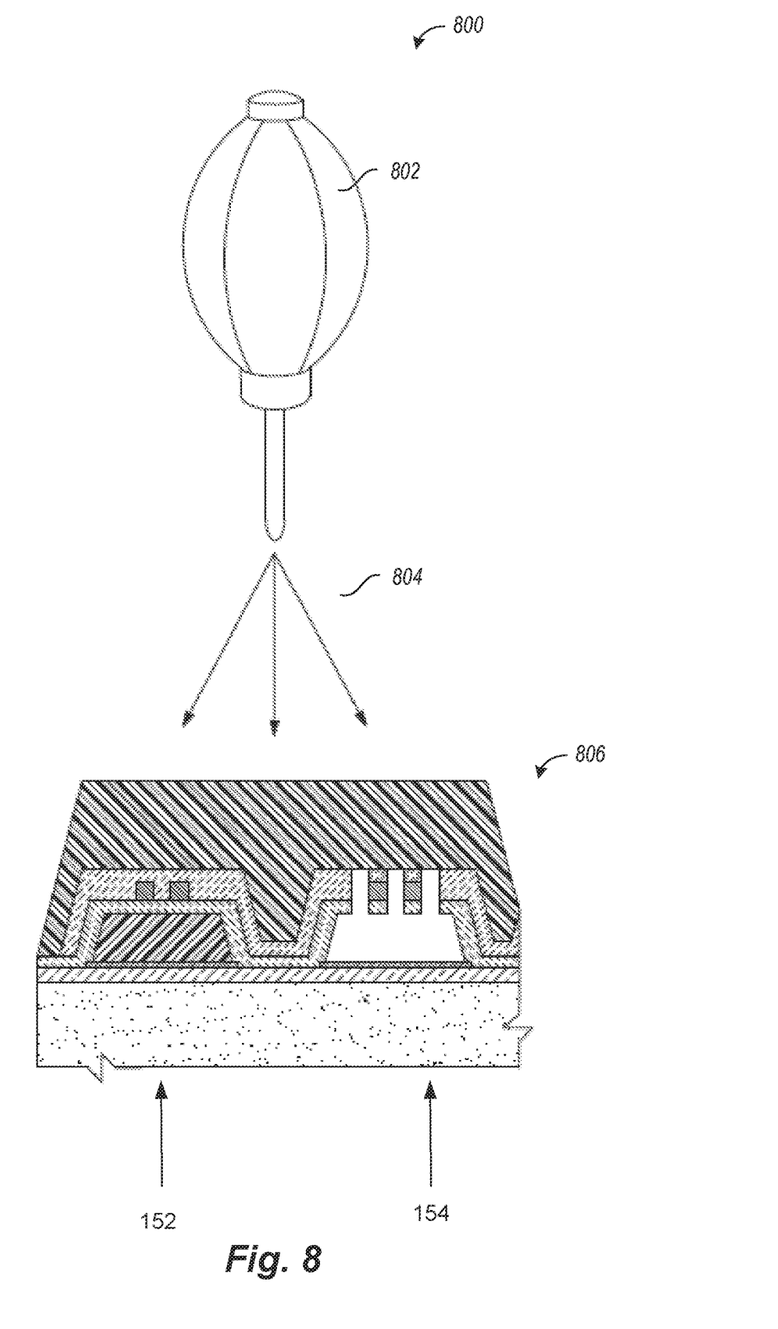
FIG. 8 is a pictorial view of a pressure sensor testing apparatus according to one embodiment.

FIG. 8 shows a pressure sensor testing apparatus 800 for measuring sensitivity of the differential capacitive pressure sensor. The pressure sensor testing apparatus includes a bellows 802 for creating a pressure disturbance 804 in the ambient environment of a differential capacitive pressure sensor module 806. The pressure sensor module 806 includes a pressure sensor 154 and a reference pressure sensor 152.

Figure 9:
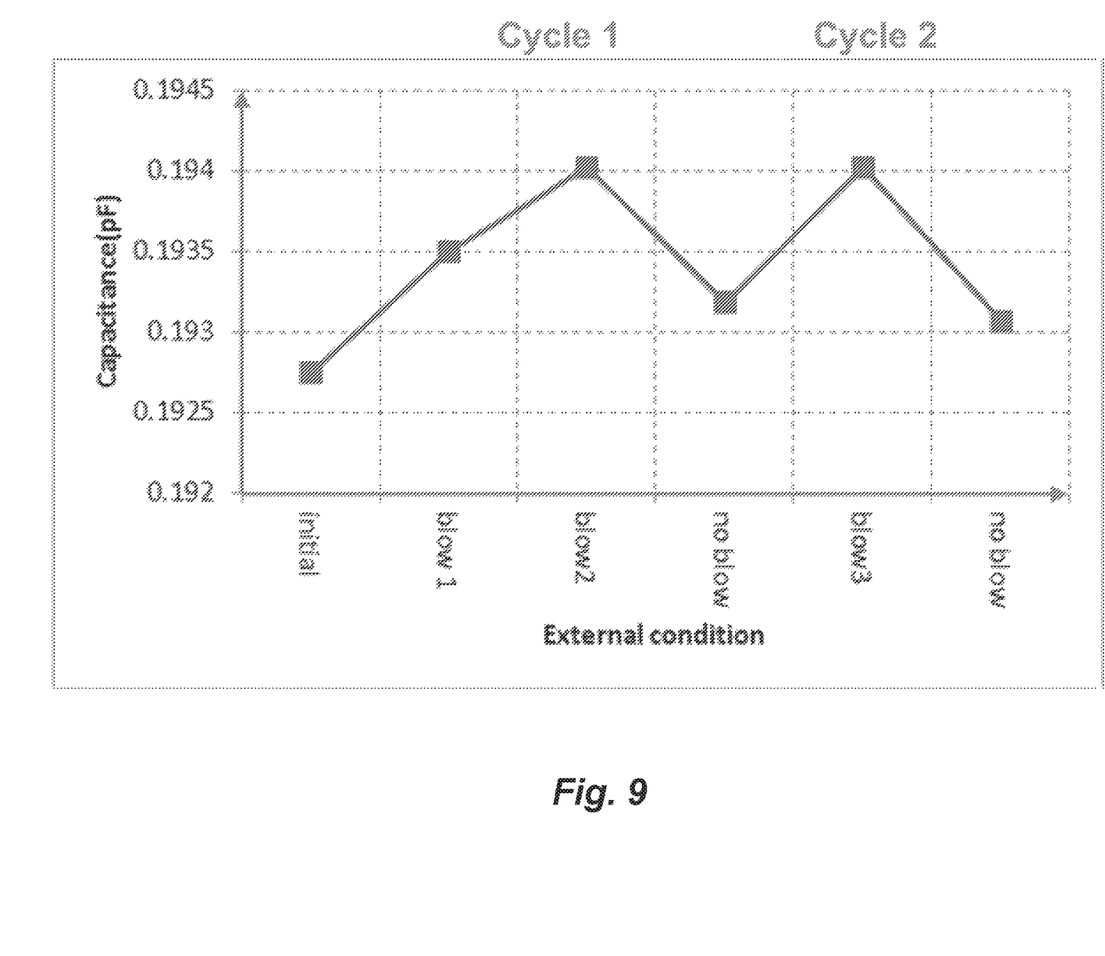
FIG. 9 is a plot of differential capacitance measurements during a test of the pressure sensor shown in FIGS. 2 and 3.

FIG. 9 is a plot of capacitance data collected from the testing apparatus 800 during a pressure sensor test. In a first cycle, the bellows 802 was used twice in succession to blow air toward the thin capacitive dielectric film 217 within the pressure sensor module 806. After the pressure disturbances ceased, the capacitance value recovered to nearly its initial level. In a second cycle, the bellows 802 was used to blow air once more toward the thin capacitive dielectric film 217 within the pressure sensor module 806. After the pressure disturbances ceased, the capacitance value again recovered to nearly its initial level.

Figure 10:
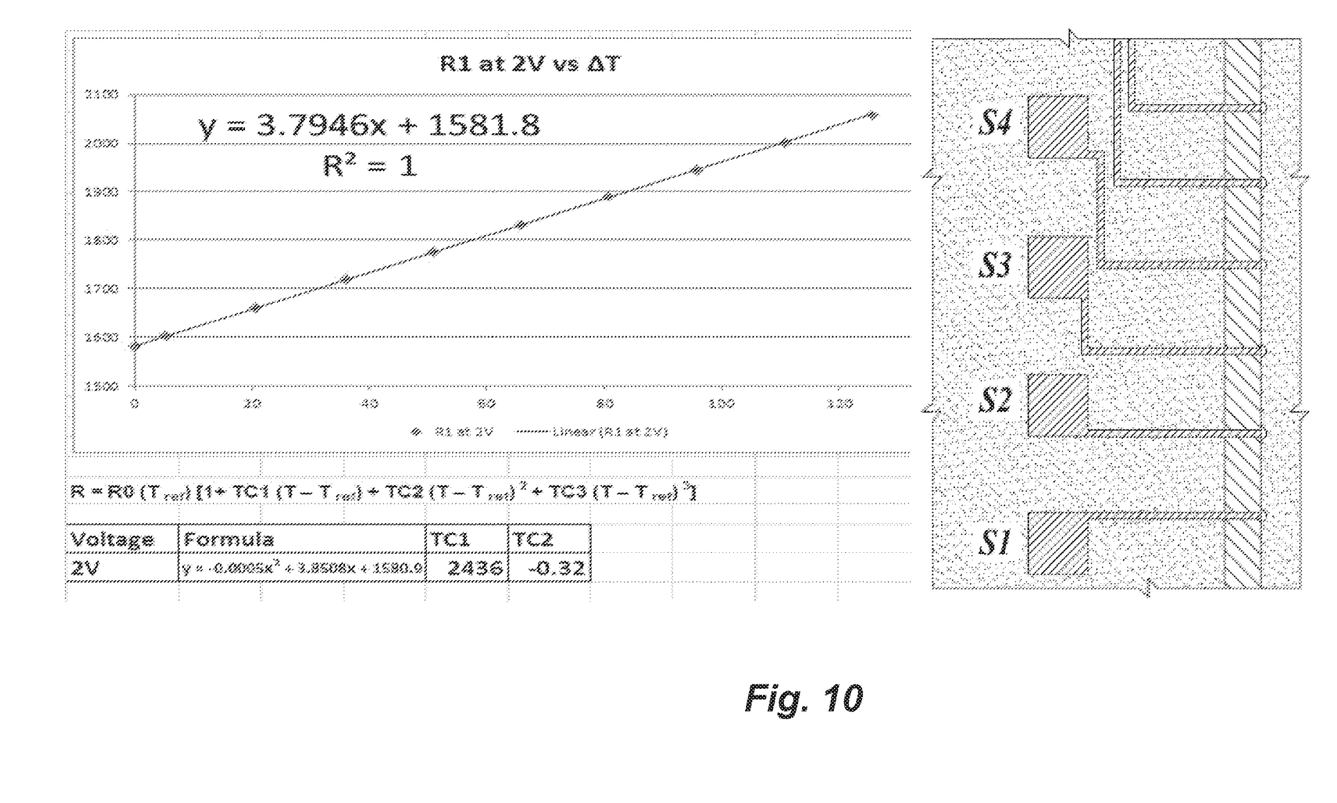
FIG. 10 is a plot of resistance as a function of temperature demonstrating linearity for a thin film platinum resistor used as a variable resistor in one embodiment of an integrated Wheatstone bridge.

FIG. 10 is a plot of experimental resistance measurements showing linear behavior of the integrated circuit Wheatstone bridge that can be used as the temperature sensor 208. The linear measurements shown, of resistance as a function of temperature, were taken using a platinum (Pt) thin film for the variable resistor $R_m$ and a chromium silicon (CrSi) thin film having low TCR, below 30 ppm, for the sensor resistor $R_p$.

Figure 11:
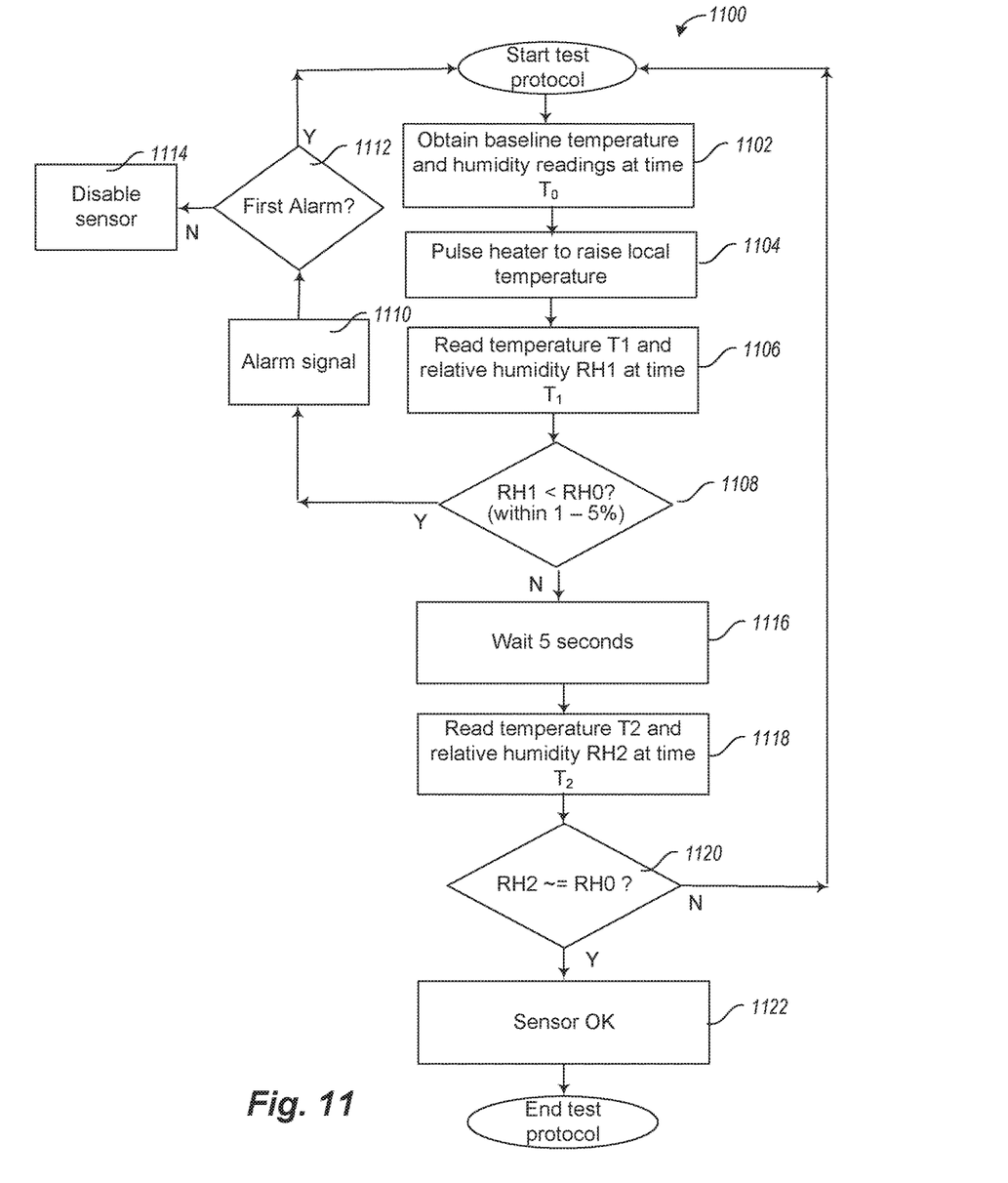
FIG. 11 is a flow diagram for a testing protocol that can be used to calibrate environmental sensors using a heater.

FIG. 11 is a flow diagram describing an exemplary test protocol 1100 which is a sequence of steps for performing a calibration test in an auto-test mode using the resistive heater 162. The test protocol 1100 as shown tests the relative humidity sensor 156 and the temperature sensor 208 by heating the local environment and taking sensor readings at selected time intervals to confirm that the sensors are responding as expected. In response to heating, the reading from the temperature sensor 208 should increase, while the relative humidity level should decrease. After switching off the heater 162 and waiting for a second time interval, the readings should return to their original values. The test protocol 1100 can be executed as follows:

At 1102, baseline temperature and humidity readings T0 and RH0, respectively, are taken at a time $T_0$.

At 1104, the heater 167 can receive a pulsed electric signal to raise the local temperature by a measurable amount. For example, the heater can be pulsed on and off every second at a current level of 20 mA for a time interval $T_1$, perhaps about one minute. Such heating would be expected to raise the detected temperature and lower the detected humidity.

At 1106, (time $T_1$) readings can be obtained from the temperature sensor 208 and the humidity sensor 156.

At 1108, the readings at time $T_1$ can be evaluated. For example, a relative humidity reading that is less than the baseline relative humidity reading but within about 1-5% indicates no change, i.e., the humidity sensor 208 is not responding. In this case, an alarm signal can be triggered at 1110. If it is determined at 1112 that the alarm is a first alarm, the test protocol 1100 may be re-started. However, if at 1112, it is determined that the alarm is a repeat alarm, continuing to indicate that the humidity sensor 156 is still not responding, the humidity sensor 156 can be disabled at 1114.

At 1116, a waiting period is set for a selected time interval, for example, 5 seconds.

At 1118, after waiting until a time $T_2$, during which the temperature can return to an ambient level, a confirmation reading can be taken at a time $T_2$.

At 1120, if the temperature and relative humidity readings at time $T_2$ have returned to substantially the same readings as at time $T_0$, the sensors are confirmed at 1122 to be working correctly, and the test protocol 1100 is complete. Readings that are substantially different from those at time $T_0$ are unexpected, causing the test protocol 1100 to be repeated.

Figure 12:
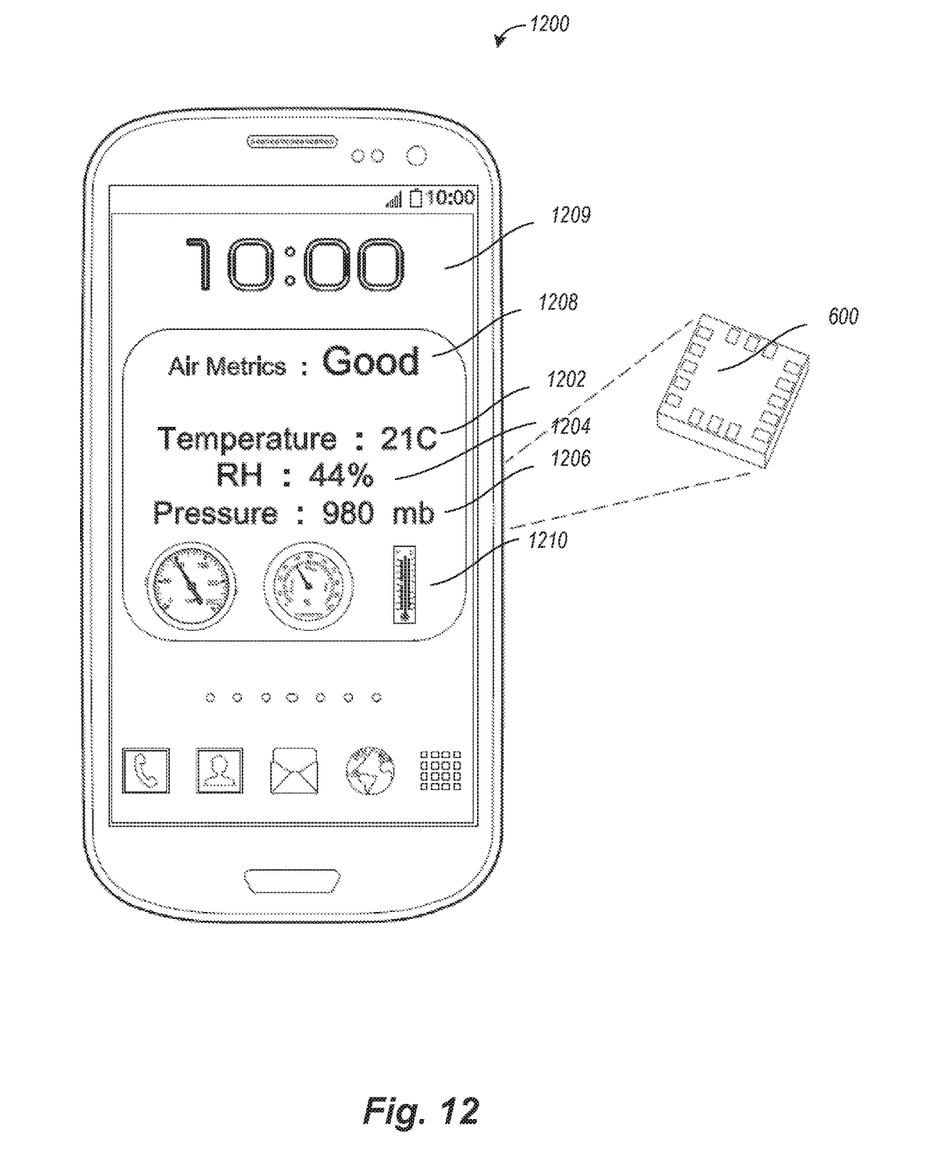
FIG. 12 is a screen shot of a smart phone running a weather station application that displays data from an on-board miniature multi-sensor module.

FIG. 12 shows a smart phone 1200 equipped with a semiconductor—based multi-sensor module 600 that can be used to monitor ambient environmental conditions in real time. A small die size and low power consumption make the multi-sensor module 600 especially suited for mobile computing applications.

A shell of the smart phone 1200 can be modified so as to allow exposure of the capacitive sensors to ambient air. An exemplary smart phone application ("app") can, for example, be programmed to display on the smart phone screen 1209 weather station icons 1210. The smart phone app can report measurements of temperature, relative humidity, and pressure, via the readouts 1202, 1204, and 1206, respectively. The smart phone app can further provide an assessment of air quality 1208 based on a comparison of the measurements to a selected standard. The standard can be pre-programmed or set by a user of the smart phone, for example.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
   forming a first sensor on a substrate, the first sensor including a first conductive layer and a first dielectric film;
   forming a second sensor on the substrate, the second sensor including a second conductive layer and a second dielectric film;
   forming a third sensor on the substrate, the third sensor including a third conductive layer and a cavity; and
   forming a fourth conductive layer on the substrate, the first conductive layer, the second conductive layer, and the third conductive layer being spaced from the fourth conductive layer by the first dielectric film, the second dielectric film, and the cavity, respectively.

2. The method of claim 1 wherein the first sensor is a first pressure sensor, the second sensor is a humidity sensor, and the third sensor is a second pressure sensor.

3. The method of claim 2 wherein the third sensor is positioned between the first sensor and the second sensor.

4. The method of claim 2, further comprising:
   forming a temperature sensor on the substrate.

5. The method of claim 4 wherein the temperature sensor includes a Wheatstone bridge.

6. The method of claim 1, further comprising:
   forming a cap that covers the first sensor and the third sensor, the cap including an opening that exposes the second sensor to an external environment.

7. The method of claim 1 wherein the first conductive layer, the second conductive layer, and the third conductive layer each include a plurality of through holes.

8. A method, comprising:
   forming a first sensor on a substrate, the first sensor including a first conductive plate having a first plurality of through holes, a second conductive plate, and a cavity that separates the first conductive plate from the second conductive plate; and
   forming a second sensor on the substrate, the second sensor including a third conductive plate having a second plurality of through holes, a fourth conductive plate, and a dielectric film that separates the third conductive plate from the fourth conductive plate.

9. The method of claim 8 wherein the second conductive plate of the first sensor and the fourth conductive plate of the second sensor are electrically coupled to each other.

10. The method of claim 8 wherein the first sensor is a pressure sensor and the second sensor is a humidity sensor.

11. The method of claim 8, further comprising:
    forming a third sensor on the substrate; and
    forming a cap on the first sensor and the third sensor, the cap including an opening that exposes the second sensor to an external environment.

12. The method of claim 11 wherein the first sensor is a pressure sensor, the second sensor is a humidity sensor, and the third sensor is a temperature sensor.

13. The method of claim 8 wherein the first plurality of through holes are arranged in a first array including a plurality of rows and columns, and the second plurality of through holes are arranged in a second array including a plurality of rows and columns.

* * * * *